United States Patent [19]

Klaue

[11] Patent Number: 4,599,999
[45] Date of Patent: Jul. 15, 1986

[54] DRILL GUIDE FOR USE WITH SURGICAL COMPRESSION PLATES

[75] Inventor: Kaj Klaue, Spiegel, Switzerland

[73] Assignee: Synthes AG, Chur, Switzerland

[21] Appl. No.: 619,488

[22] Filed: Jun. 11, 1984

[51] Int. Cl.⁴ ............................................. A61F 5/04
[52] U.S. Cl. ............................ 128/92 EB; 128/92 D
[58] Field of Search ............... 128/92 EB, 92 D, 92 E

[56] References Cited

U.S. PATENT DOCUMENTS

| 2,294,303 | 8/1942 | Jagow | 128/92 EB |
| 2,697,433 | 12/1954 | Zehnder | 128/92 EB |
| 4,388,921 | 6/1983 | Sutter et al. | 128/92 D |
| 4,493,317 | 1/1985 | Klaue | 128/92 EB |
| 4,528,980 | 7/1985 | Kenna | 128/92 EB |

Primary Examiner—Gene Mancene
Assistant Examiner—C. W. Shedd
Attorney, Agent, or Firm—Davis Hoxie Faithfull & Hapgood

[57] ABSTRACT

A drill guide for use with surgical compression plates having means to prevent the drill from contacting the sides of the plate holes when drilling obliquely.

2 Claims, 5 Drawing Figures

DRILL GUIDE FOR USE WITH SURGICAL COMPRESSION PLATES

The invention relates to a drill guide for use with compression plates applied to stabilize fractured bones in compression osteosynthesis; or in connection with osteotomies.

In compression osteosynthesis a compression plate is conventionally mounted opposite the area to be stabilized on the side of the bone to be tensioned by means of screws perpendicular to the longitudinal axes of the bone and plate.

Recently it has also been proposed that stabilization by means of a plate could be improved through addition of an inclined tension screw, running obliquely to the longitudinal axes of the bone and plate, that penetrated through the fracture plane; the axial force of said screw produces additional interfragmentary compression. (See Claudi et al., Hel. Chir. Acta 46, (1979) p. 178 and FIG. 2B).

For utilization of the last mentioned method it is necessary to apply a compression plate which permits sufficient tilting of the screws in the holes of the compression plates with reference to a plane transverse to the axis of the plate, and which, in addition, permits some longitudinal movement of the screw in a tilted and fully screwed-in position, particularly when the screw is threaded along its entire length.

In my copending U.S. patent application Ser. No. 321,602 filed Nov. 16, 1981, now U.S. Pat. No. 4,493,317, and in my European patent application 81 81 0467.1 filed Nov. 20, 1981 and published June 16, 1982, there are disclosed compression plates specifically adapted for the oblique insertion of screws. The elongated holes of such plates, at least on the side nearest the bone, are undercut to facilitate such oblique insertion of the screws.

In using plates like those disclosed in the prior patent applications referred to it is desirable, in drilling through the plate holes into the bone, that drill guides be used to be sure that the holes are properly positioned relative to the plate, and at a constant and proper inclination. Suitable drill guides are disclosed in the earlier applications. One of these has a spherical bearing element adapted to rest in the plate slot. The other has an elongated bearing element.

Certain difficulties have arisen with respect to the drill guides shown in my prior applications. For example, when the drill guide is tilted to provide for a hole having an oblique or slanted axis, it sometimes happens that the guide is inclined too far. The drill then bears against the edge or chamfered surface of the hole at the bottom of the plate. This renders the plate imperfect and creates a focal point for corrosion.

Also in the devices shown in the prior applications, no provision was made for removing bone turnings from the guide. The accumulation of bone turnings can cause problems.

In accordance with the present invention a collar is provided around the drill shaft on the bearing surface of the guide, to limit angular displacement of the guide, and prevent damage to the plate. In addition a cut out section is provided in the drill guide to permit turnings to be eliminated from the system.

Although my European patent application mentions the possibility of a stop to prevent too wide an excursion of the drill guide, no specific structure is described therein.

Specifically, a drill guide according to the invention comprises a elongated body having a bearing section with a rounded hemispherical surface, a guide hole or shaft positioned eccentrically with respect to the longitudinal axis of the guide and extending through the body with an opening in the surface of the bearing member, and a collar surrounding said opening of said shaft and extending beyond the surface of the bearing member. Further in a drill guide according to the invention, an arcuate section of the body of the guide is cut out, the cut out section intersecting the shaft, to provide a means for removing bone turnings carried up the shaft by a drill.

The invention will be further described in connection with the accompanying drawings in which.

Figure 1:
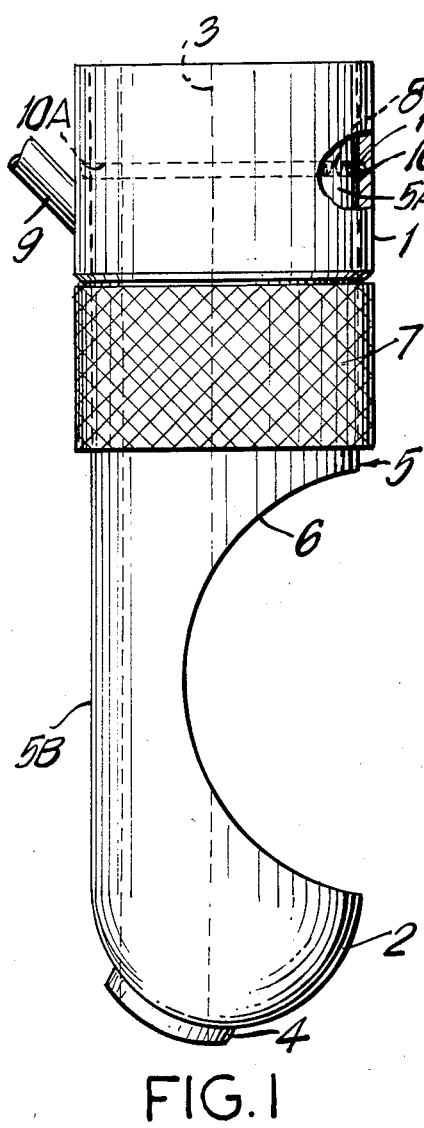
FIG. 1 is a view in side elevation of a preferred embodiment of a drill guide according to the invention.

Referring to the drawings, a drill guide according to the invention has a body 5 with a cylindrical upper section 5A and a reduced lower section 5B, terminating in a rounded bearing section 2.

A vertical shaft 3 extends through the body 5, eccentric to the axis of the body. In the side of the body 5 is a rounded arcuate opening 6, the radius of the opening being larger than the transverse width of the body, thereby exposing the shaft 3 and allowing drill chips or turnings to be removed.

A cylindrical casing 1 is rotatably fitted over the upper portion 5A of the body 5. The upper portion 5A is provided with a socket 11 in which rests a helical spring 8 and a ball bearing 10, the bearing being slightly wider than the aperture of the socket 11 which is peened around its periphery after insertion of the spring and bearing to retain the ball bearing. The bearing cooperates with a circular groove 10A located on the inner surface of casing 1 to retain the casing on the body 5, while permitting the casing to be rotated about the body 5.

Immediately below the casing 1, a milled cuff 7 is fixed to the upper section of the guide body to facilitate gripping the guide.

Figure 2:
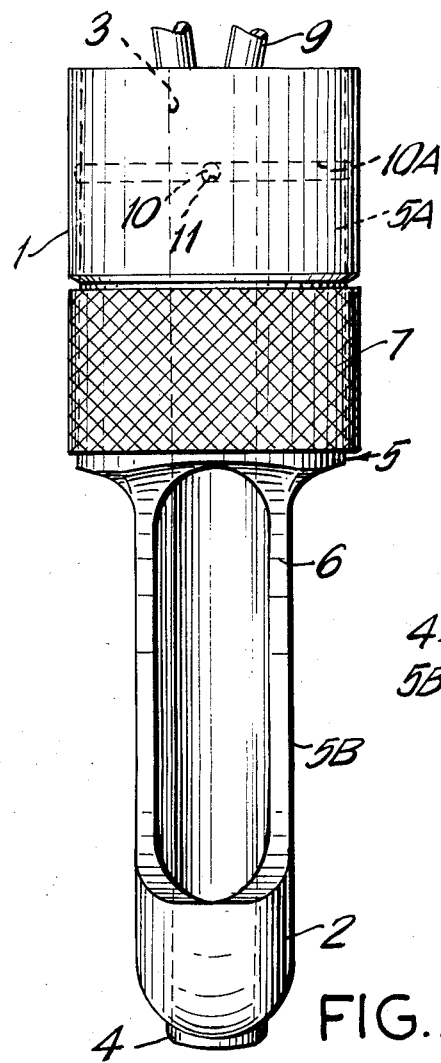
FIG. 2 is a front elevational view of the drill guide of FIG. 1.
Figure 3:
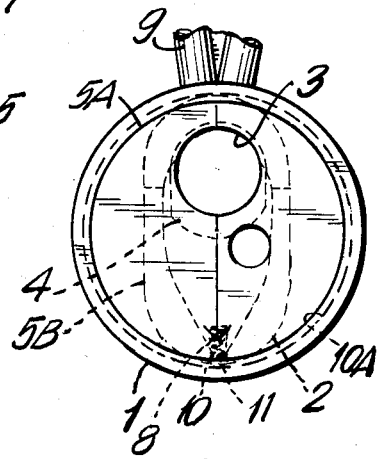
FIG. 3 is a plan view of the drill guide of FIG. 1.

A handle 9, shown only in part in FIGS. 1–3 is welded on the casing 1.

In accordance with the invention, the bearing section 2 of the body 5 has a collar 4 surrounding the opening of shaft 3 in the surface of the bearing section 2. The function of the collar 4 is illustrated in FIGS. 4 and 5.

Figure 4:
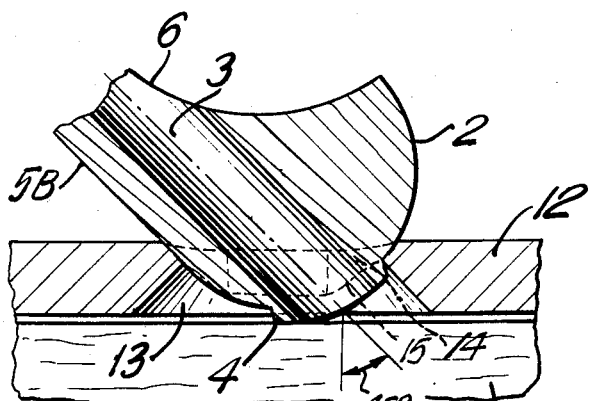
FIG. 4 and FIG. 5 are views in vertical section of the bearing section of a drill guide according to the invention resting in a compression plate.

Referring first to FIG. 4, the drill guide of the invention is shown being used with a surgical compression plate 12 of the type disclosed and claimed in my prior applications referred to above. Such plates have a series of elongated holes as at 14, each of the holes having an inclined upper camming surface 15 and an undercut lower surface 13 on the side of the plate to be placed in contact with bone. As shown in FIG. 4, if it is desired to form a hole at an angle of 45°, in a bone 16 underlying the plate 12, the drill guide is rotated or rocked until the shaft 3 assumes that angle, the bearing section 2 rotating against the camming surface 15 of the plate hole. The collar 4 comes into contact with the undercut surface 13 and prevents the guide being inclined further, thus also preventing a drill (not shown), inserted through shaft 3, from bearing against the undercut surface of the plate and assuring that an angle of 45° will be obtained.

Figure 5:
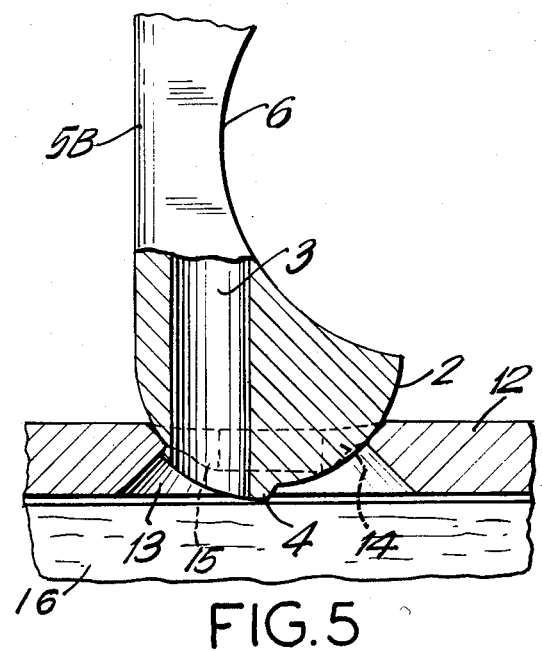

In FIG. 5, the guide is rotated to drill a vertical hole. Again the collar 4 bears against the plate surface 13 and serves to insure that the guide is oriented correctly and that the plate is not damaged. The hole drilled in the bone will be precisely normal to the plate surface.

What I claim is:

1. A drill guide for angularly aligning and guiding a drill with respect to an elongated hole in a bone plate, said elongated hole having an inwardly inclined upper camming surface and undercut lower surfaces on the side of the plate to be placed in contact with a bone, said drill guide comprising:

an elongated body having at least one hemispherical end surface which bears against the inclined upper surface of said elongated hole and is adapted to be rocked in a plane aligned with the long axis of said plate hole, a guide hole extending through said body which is eccentric to the axis of said body, and a protuberant collar extending from said end surface around the end of said guide hole to form an extension of said guide hole, the walls of said collar being adapted to bear against the undercut surfaces of said plate hole to limit the angular travel of said drill guide when it is rocked in said plate hole.

2. The drill guide claimed in claim 1 and wherein the body of the guide has an arcuate lateral opening for the removal of chips.

* * * * *